United States Patent
Chono

(10) Patent No.: US 8,419,641 B2
(45) Date of Patent: Apr. 16, 2013

(54) MEDICAL IMAGE DISPLAY METHOD, MEDICAL IMAGE DIAGNOSTIC APPARATUS, AND MEDICAL IMAGE DISPLAY DEVICE

(75) Inventor: Tomoaki Chono, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 13/201,392

(22) PCT Filed: Feb. 8, 2010

(86) PCT No.: PCT/JP2010/051765
§ 371 (c)(1),
(2), (4) Date: Aug. 12, 2011

(87) PCT Pub. No.: WO2010/092919
PCT Pub. Date: Aug. 19, 2010

(65) Prior Publication Data
US 2011/0301454 A1    Dec. 8, 2011

(30) Foreign Application Priority Data

Feb. 13, 2009 (JP) .................................. 2009-030739

(51) Int. Cl.
*A61B 8/00* (2006.01)
(52) U.S. Cl.
USPC ........... 600/437; 600/410; 600/407; 382/128; 382/131; 382/132
(58) Field of Classification Search .......... 600/407–429, 600/437–469; 382/128–132
See application file for complete search history.

(56) References Cited

U.S. PATENT DOCUMENTS

| | | | | |
|---|---|---|---|---|
| 6,901,284 | B1* | 5/2005 | Maki et al. | 600/476 |
| 6,957,095 | B2* | 10/2005 | Matsui | 600/407 |
| 7,047,149 | B1* | 5/2006 | Maki et al. | 702/150 |
| 7,079,140 | B2* | 7/2006 | Boehler et al. | 345/440 |
| 7,359,825 | B2* | 4/2008 | Maki et al. | 702/150 |
| 7,804,988 | B2* | 9/2010 | Flohr et al. | 382/128 |
| 7,853,058 | B2* | 12/2010 | Gauldie et al. | 382/128 |
| 8,126,227 | B2* | 2/2012 | Fujisawa | 382/128 |
| 8,199,984 | B2* | 6/2012 | Mori et al. | 382/128 |
| 8,238,626 | B2* | 8/2012 | Matsue et al. | 382/128 |

(Continued)

FOREIGN PATENT DOCUMENTS

| | | |
|---|---|---|
| JP | 03-016556 | 1/1991 |
| JP | 09-187448 | 7/1997 |

(Continued)

*Primary Examiner* — Sanjay Cattungal
(74) *Attorney, Agent, or Firm* — Brundidge & Stanger, P.C.

(57) ABSTRACT

Disclosed is a medical image display method for displaying a tomographic image obtained by scanning an image of a cross-section of an organ of an object and finding the volume of an inner cavity region surrounded by the inner wall surface of the inner cavity of the organ on the basis of the displayed tomographic image, comprising a step that segmentizes the inner cavity region into a first inner cavity region and a second inner cavity region, a step that calculates volume of the first inner cavity using the disk method, a step that calculates volume of the second inner cavity region using the pseudo disk method, a step that calculates the entire inner cavity volume by summing the calculated volumes of the first and the second inner cavity, and a step that displays the first and the second inner cavity volumes and/or the entire inner cavity volume.

15 Claims, 12 Drawing Sheets

U.S. PATENT DOCUMENTS

| | | | |
|---|---|---|---|
| 2002/0183606 A1* | 12/2002 | Boehler et al. | 600/407 |
| 2003/0069503 A1* | 4/2003 | Matsui | 600/437 |
| 2004/0254475 A1* | 12/2004 | Maki et al. | 600/473 |
| 2006/0178839 A1* | 8/2006 | Maki et al. | 702/19 |
| 2006/0270912 A1* | 11/2006 | Villain et al. | 600/300 |
| 2007/0040831 A1* | 2/2007 | Flohr et al. | 345/424 |
| 2008/0117210 A1* | 5/2008 | Razeto et al. | 345/424 |
| 2008/0118117 A1* | 5/2008 | Gauldie et al. | 382/128 |
| 2008/0130824 A1* | 6/2008 | Fujisawa | 378/4 |
| 2008/0219537 A1* | 9/2008 | Matsue et al. | 382/131 |
| 2009/0161927 A1* | 6/2009 | Mori et al. | 382/128 |
| 2009/0174729 A1* | 7/2009 | Matsumoto | 345/619 |
| 2009/0198133 A1* | 8/2009 | Kawagishi et al. | 600/443 |
| 2010/0092052 A1* | 4/2010 | Declerck et al. | 382/128 |
| 2011/0123077 A1* | 5/2011 | Goto | 382/128 |
| 2011/0172516 A1* | 7/2011 | Sugiura | 600/410 |
| 2011/0301454 A1* | 12/2011 | Chono | 600/425 |
| 2012/0027276 A1* | 2/2012 | Chono | 382/128 |
| 2012/0053408 A1* | 3/2012 | Miyamoto | 600/109 |
| 2012/0119096 A1* | 5/2012 | Vija et al. | 250/370.08 |
| 2012/0190967 A1* | 7/2012 | Nahm | 600/411 |

FOREIGN PATENT DOCUMENTS

| | | |
|---|---|---|
| JP | 2003-310616 | 11/2003 |
| JP | 2004-073850 | 3/2004 |
| JP | 2006-167080 | 6/2006 |

* cited by examiner

MEDICAL IMAGE DISPLAY METHOD, MEDICAL IMAGE DIAGNOSTIC APPARATUS, AND MEDICAL IMAGE DISPLAY DEVICE

FIELD OF THE INVENTION

The present invention relates to a medical image display method, medical image diagnostic apparatus and medical image display device, particularly to a technique for measuring volume of a cardiac chamber, etc. of an object to be examined with high accuracy using the disk method.

DESCRIPTION OF RELATED ART

An ultrasonic diagnostic apparatus, X-ray CT apparatus or magnetic resonance imaging (MRI) apparatus are commonly known as a conventional medical image diagnostic apparatus that scan the tissues, etc. of an examination region in an object and display a tomographic image thereof. For example, an ultrasonic diagnostic apparatus constructs a cross-sectional image such as a B-mode image by transmitting ultrasonic waves to the inside of an object and receiving reflected echo signals of the ultrasonic waves from the inside of the object in accordance with the constitution of the biological tissues by an ultrasonic probe.

In such medical image diagnostic apparatuses, volume measurement is to be executed on a cardiac chamber of the object such as a left ventricle or a left atrium that are communicated via a cardiac valve. Volume measurement here is to calculate volume of the region encompassed by the inner wall surface of the cardiac chamber and the valve ring surface using the Area Length method or the Modified Simpson method (disk method). Both of the forementioned clinical examination methods are commonly used and are capable of calculating the volume simply and quickly from a 2-dimensional image by assuming that a cardiac chamber is a body of revolution.

More specifically, in the disk method, by tracing the portion, for example which is equivalent to the inner wall surface of the cardiac chamber on a tomographic image of a heart displayed on a display unit via an input interface, a valve ring line which is equivalent to the valve ring surface of the heart is generated by connecting both end points of the trace line, and a cardiac chamber axis is generated by connecting the center of the valve ring line and the position which is the farthest from the inner wall trace line of the cardiac chamber. Further, disk volume is obtained by sectionalizing the cardiac chamber region into plural portions by a plurality of partition lines that are perpendicular to the cardiac chamber axis and assuming the respective sectionalized portions as a disk, and summation of the respective disk volumes is calculated as the volume of the cardiac chamber.

In Patent Document 1, a technique is disclosed for detecting regional wall motion abnormality of a heart by cutting off a part of the disk in the vertical direction to the disk surface so as to calculate a partial volume, which leads to calculation of regional volumetric change of a heart.

PRIOR ART DOCUMENTS

Patent Document 1: Japanese Patent No. 3723149

However, the technique disclosed in Patent Document 1 does not consider the case that the valve ring surface and the cardiac chamber axis are not vertical to each other for calculating the volume of a cardiac chamber with high accuracy.

More specifically, while it is assumed that the valve ring surface (valve ring line) and the cardiac chamber axis are vertical to each other in the commonly known disk method represented in Patent Document 1, there are cases that they are not vertical to each other due to technical difficulty in scanning of a heart. In these cases, while the volume can be calculated with high accuracy in the region where both ends of the partition line generated vertically to the cardiac chamber axis intersect with the inner wall surface of the cardiac chamber, since disk volume of the region where one end of the partition line intersects with the inner wall of the cardiac chamber and the other end intersects with the valve ring surface is calculated smaller than the actual volume or there is a region where a disk itself is not generated due to the cardiac chamber axis being discontinued by the valve ring surface, the entire volume is calculated smaller than the actual volume.

Because the volume of a cardiac chamber is a significant diagnostic material for detecting abnormality of the shape or function of a heart, calculation of the volume with higher accuracy is required.

Given this factor, the objective of the present invention is to calculate volume of a cardiac chamber with higher accuracy even in the case that the valve ring surface and the cardiac chamber axis are not vertical to each other.

BRIEF SUMMARY OF THE INVENTION

The medical image display method of the present invention displays the tomographic image acquired by scanning the cross-section of an organ of an object on a display unit, and obtains volume of the inner cavity region encompassed by the inner wall surface of the inner cavity of an organ based on the displayed tomographic image. The medical image display method of the present invention is characterized in comprising:

a step that traces and displays the portion equivalent to the inner wall surface of the inner cavity on a tomographic image;

a step that displays the line which connects both end points of the traced inner cavity trace line;

a step that displays the inner cavity axis which passes through the center of the line and the position farthest from the center of the inner cavity trace line;

a step that displays a plurality of partition lines which are orthogonal to the inner cavity axis and of which their both ends intersect with the inner cavity trace line;

a step that calculates inner cavity volume of a first inner cavity region formed by a plurality of partition lines using the disk method;

a step that calculates inner cavity volume of a second inner cavity region encompassed by the partition line closest to the line from among the plurality of partition lines, the line and an inner cavity trace line using the pseudo disk method;

a step that calculates the entire inner cavity volume by the sum of the calculated first and second inner cavity regions; and a step that displays the inner cavity volume of the first and second inner cavity regions and/or the volume of the entire inner cavity region.

Also, the medical image display method of the present invention displays the tomographic image acquired by scanning the cross-section of a heart of an object on a display unit, and obtains volume of the cardiac chamber region encompassed by the inner wall surface of the cardiac chamber of a heart based on the displayed tomographic image.

The medical image display method of the present invention is characterized in comprising:

a step that traces and displays the portion equivalent to the inner wall surface of a cardiac chamber on a tomographic image;

a step that displays the valve ring line equivalent to the valve ring surface by connecting both end points of the traced inner wall trace line of the cardiac chamber;

a step that displays the cardiac chamber axis which passes through the center of the valve ring line and the position farthest from the center of the inner wall trace line of the cardiac chamber;

a step that displays a plurality of partition lines which are orthogonal to the cardiac chamber axis and of which their both ends intersect with the inner wall trace line of the cardiac chamber;

a step that calculates cardiac chamber volume of a first cardiac chamber region formed by a plurality of partition lines using the disk method;

a step that calculates cardiac chamber volume of a second cardiac chamber region encompassed by the partition line closest to the valve ring line from among the plurality of partition lines, the valve ring line and an inner wall trace line of the cardiac chamber using the pseudo disk method;

a step that calculates volume of the entire cardiac chamber by the sum of the calculated first and second cardiac chamber regions; and a step that displays the volume of the first and second cardiac chamber regions and/or the volume of the entire cardiac chamber region.

In other words, while volume of the region where both ends of the partition lines intersect with the inner wall trace line of the cardiac chamber (the first cardiac chamber region) is calculated using the conventional disk method, volume of the region encompassed by the partition line closest to the valve ring line, the valve ring line and the inner wall trace line of the cardiac chamber and the volume may be calculated smaller than the actual volume when the common disk method is used (the second cardiac chamber region) is calculated using the pseudo disk method. In this manner, volume of both first cardiac chamber region and second cardiac chamber region can be obtained with high accuracy, thus the sum of these volumes can be accurately calculated as the volume of the entire cardiac chamber region.

The step for calculating volume of the second cardiac chamber region includes:

a step that generates a virtual trace line that forms the second cardiac chamber region which faces the region sandwiched by the cardiac chamber inner wall trace line and the cardiac chamber axis;

a step that generates a plurality of virtual partition lines that are orthogonal to the cardiac chamber axis, their one end intersects with the virtual trace line and the other end intersects with the inner wall trace line of the cardiac chamber;

a step that generates a virtual disk based on the virtual trace line, virtual partition lines and inner wall trace line of the cardiac chamber; and a step that calculates volume of the partial disk of the side where the inner wall trace line of the cardiac chamber is included as the cardiac chamber volume of the second cardiac chamber region by cutting off the virtual disk by the valve ring surface, and is capable of displaying the virtual trace line and the virtual partition lines on a display unit.

In this manner, a virtual disk is generated using a virtual trace line and virtual partition lines for the second cardiac region, and volume thereof is calculated by setting the part which needs the virtual disk (the side of disk being cut off by a valve ring surface including the inner wall trace line of the cardiac chamber) as the partial disk. By using such pseudo disk method, it is possible to calculate volume of the second region where the volume may be calculated smaller than the actual volume when the common disk method is applied with high accuracy.

The medical image diagnostic apparatus of the present invention is configured comprising:

a display unit configured to display a tomographic image acquired by scanning a cross section of an organ in an object to be examined; and a calculation unit configured to obtain volume of an inner cavity region encompassed by the inner wall surface of the inner cavity of the organ based on the tomographic image displayed on the display unit. The medical image diagnostic apparatus of the present invention is characterized in comprising:

means that traces the portion equivalent to the inner wall surface of an inner cavity of an organ on the tomographic image displayed on a display unit;

means that generates and displays the line connecting both end points of the traced inner cavity trace line;

means that generates and displays the inner cavity axis passing through the center of the line and the position farthest from the center of the inner cavity trace line;

means that generates and displays a plurality of partition lines that are orthogonal to the inner cavity axis and of which their both ends intersect with the inner cavity trace line;

means that calculates inner cavity volume of a first inner cavity region formed by the plurality of partition lines using the disk method;

means that calculates inner cavity volume of a second inner cavity region encompassed by the partition line closest to the line from among the plurality of partition lines, the line and the inner cavity trace line using the pseudo disk method;

means that calculates volume of the entire inner cavity by the sum of the calculated first and second inner cavity regions; and means that displays the volume of the first and second inner cavity regions and/or the volume of the entire inner cavity region.

The medical image diagnostic apparatus of the present invention is also configured comprising:

a display unit configured to display a tomographic image acquired by scanning a cross section of a heart in an object to be examined; and a calculation unit configured to obtain volume of the cardiac chamber region encompassed by the inner wall surface of the cardiac chamber and the valve ring surface based on the tomographic image displayed on the display unit. The medical image diagnostic apparatus of the present invention is characterized also in comprising:

means that traces the portion equivalent to the inner wall surface of a cardiac chamber of a heart on the tomographic image displayed on a display unit;

means that generates and displays the valve ring line equivalent to the valve ring surface by connecting both end points of the traced inner cavity trace line the cardiac chamber;

means that generates and displays the cardiac chamber axis passing through the center of the valve ring line and the position farthest from the center of the inner wall trace line of the cardiac chamber;

means that generates and displays a plurality of partition lines that are orthogonal to the cardiac chamber axis and of which their both ends intersect with the inner wall trace line of the cardiac chamber;

means that calculates cardiac chamber volume of a first cardiac chamber region formed by the plurality of partition lines using the disk method;

means that calculates volume of a second cardiac chamber region encompassed by the partition line closest to the valve ring line from among the plurality of partition lines, the valve ring line and the inner wall trace line of the cardiac chamber using the pseudo disk method;

means that calculates volume of the entire cardiac chamber by the sum of the calculated first and second cardiac chamber regions; and means that displays the volume of the first and second cardiac chamber regions and/or the volume of the entire cardiac chamber region.

The medical image display device of the present invention displays the tomographic image acquired by scanning the cross-section of a heart of an object on a display unit, and obtains volume of the cardiac chamber region encompassed by the inner wall surface of the cardiac chamber and the valve ring surface of a heart based on the displayed tomographic image. The medical image is configured having:

a cardiac chamber border line formed by the inner wall trace line of the cardiac chamber equivalent to the inner wall surface and the valve ring line equivalent to the valve ring surface;

a cardiac chamber axis that passes through the center of the valve ring line and the position farthest from the center of the inner wall trace line of the cardiac chamber; and an image on which a plurality of partition lines orthogonal to the cardiac chamber axis are displayed. Particularly, a first cardiac chamber region where both ends of the partition lines intersect with the inner wall trace line of the cardiac chamber and a second cardiac chamber region wherein one end of the partition line intersects with the valve ring line and the other end intersects with the inner wall trace line of the cardiac chamber can be displayed in different display patterns.

EFFECT OF THE INVENTION

In accordance with the present invention, it is possible to calculate volume of a cardiac chamber with high accuracy even in the case that the valve ring surface and the cardiac chamber axis are not vertical to each other.

BRIEF DESCRIPTION OF THE DIAGRAMS

DETAILED DESCRIPTION OF THE INVENTION

An embodiment of the medical image diagnostic apparatus and the medical image display device to which the present invention is applied will be described below. In the present embodiment, an ultrasonic diagnostic apparatus will be exemplified as an example of a medical image diagnostic apparatus and a medical image display device. The present embodiment can also be applied to other devices for imaging the tissues of an examination region in an object and displaying a tomographic image, etc. such as an X-ray CT apparatus or a magnetic resonance imaging (MRI) apparatus.

Figure 1:
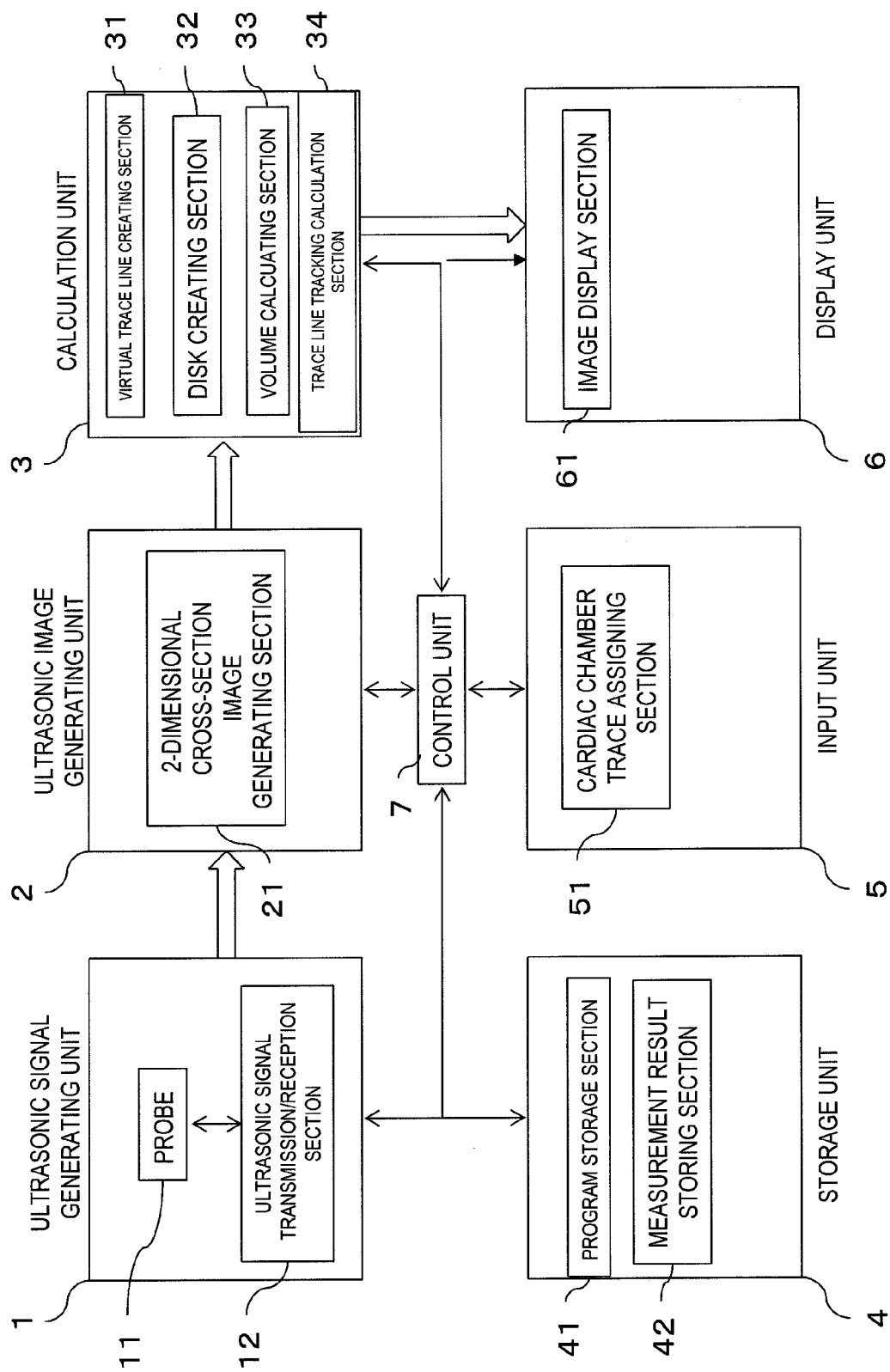
FIG. 1 is a block diagram showing the outline of general configuration of an ultrasonic diagnostic apparatus in the present embodiment.

FIG. 1 shows a block diagram showing the outline of general configuration of an ultrasonic diagnostic apparatus in the present embodiment. As shown in FIG. 1, the ultrasonic diagnostic apparatus comprises an ultrasonic signal generation unit 1 configured to transmit/receive ultrasonic waves to/from an object to be examined, an ultrasonic image generation unit 2 configured to generate an ultrasonic image from the ultrasonic signals, a calculation unit 3 configured to generate a trace line or a disk or to calculate volume of a cardiac chamber, a storage unit 4 configured to store a program or a measurement result, input unit 5 configured to specify the contour position of a cardiac chamber, a display unit 6 configured to display a measurement value or a result image, and a control unit 7 configured to control the entire apparatus. Solid arrows indicate control, and outlined arrows indicate flow of image signal data.

The ultrasonic signal generation unit 1 generates ultrasonic signals by transmitting/receiving ultrasonic waves to/from the object, and comprises a probe 11 and an ultrasonic transmission/reception section 12. The probe 1 is a device that transmits/receives ultrasonic waves and converts them into electronic signals, having scanning methods such as a linear type, convex type or sector type. The ultrasonic signal transmission/reception section 12 transmits/receives electrified ultrasonic signals to/from the probe. It acquires ultrasonic signals by passing the received signals through a phasing circuit.

The ultrasonic image generation unit 2 generates an ultrasonic image based on the scan setting of the apparatus from the signals inputted from the ultrasonic signal generation unit 1, and comprises a 2-dimensional cross-section image generation section 21. The 2-dimensional cross-section image generation section 21 generates a tomographic image such as a B-mode image from the ultrasonic signals acquired by scanning a cross-section of an examination region such as a heart of the object.

The calculation unit 3 generates a trace line or a disk for applying the disk method for volume calculation, and comprises a virtual trace line generation section 31, a disk generation section 32, a volume calculation section 33 and a trace line tracking calculation section 34.

The virtual trace line generation section 31 executes calculation for generating a virtual trace line so as to generate a disk for filling a cardiac chamber by for example, extending the inner wall trace line of the cardiac chamber which is the contour of the inner wall surface of the cardiac chamber.

The disk generation section 32 executes calculation for generating a disk using an inner wall trace line of a cardiac chamber, a virtual trace line and a valve ring surface. The volume calculation section 33 calculates volume of the generated disk and obtains the summation as the cardiac chamber volume. The trace line tracking calculation section 34 calculates the changed cardiac chamber contour position by tracking the position of the trace line for each frame.

The storage device 4 is for storing an algorithm in the calculation unit 3 or a program for controlling the respective units or for storing calculation result or ultrasonic signals, which is a storage device such as a hard disk, semiconductor memory or optical disk, comprising a program storage section 41 and a measurement result storage section 42.

The program storage section 41 stores the program in which algorithms such as virtual trace line generation, disk generation, volume calculation or trace line tracking calculation in the calculation unit 3 are inscribed or the program for controlling the respective units. The measurement result storage section 42 stores the measurement result data calculated by the calculation unit 3, and stores the ultrasonic signal data, etc. outputted from each unit.

The input unit 5 comprises a cardiac chamber trace specifying section 51. The cardiac chamber trace specifying section 51 can be the input interface such as a keyboard, trackball or switch as the input device for tracing, for example the position equivalent to the inner wall surface of the cardiac chamber on a tomographic image, and capable of tracing by the full automatic processing. It also comprises the method that an examiner specifies a several points of positions equivalent to the inner wall surface of the cardiac chamber and executes tracing on the basis of the specified positions or an interface for manual setting.

The display unit 6 comprises the interface that displays and outputs a measurement value or an image, and an image display section 61 displays the B-mode image outputted from the ultrasonic image generation unit 2 and the disk or the volume value generated by the calculation unit on a screen.

(Operation by an Examiner)

Figure 2:
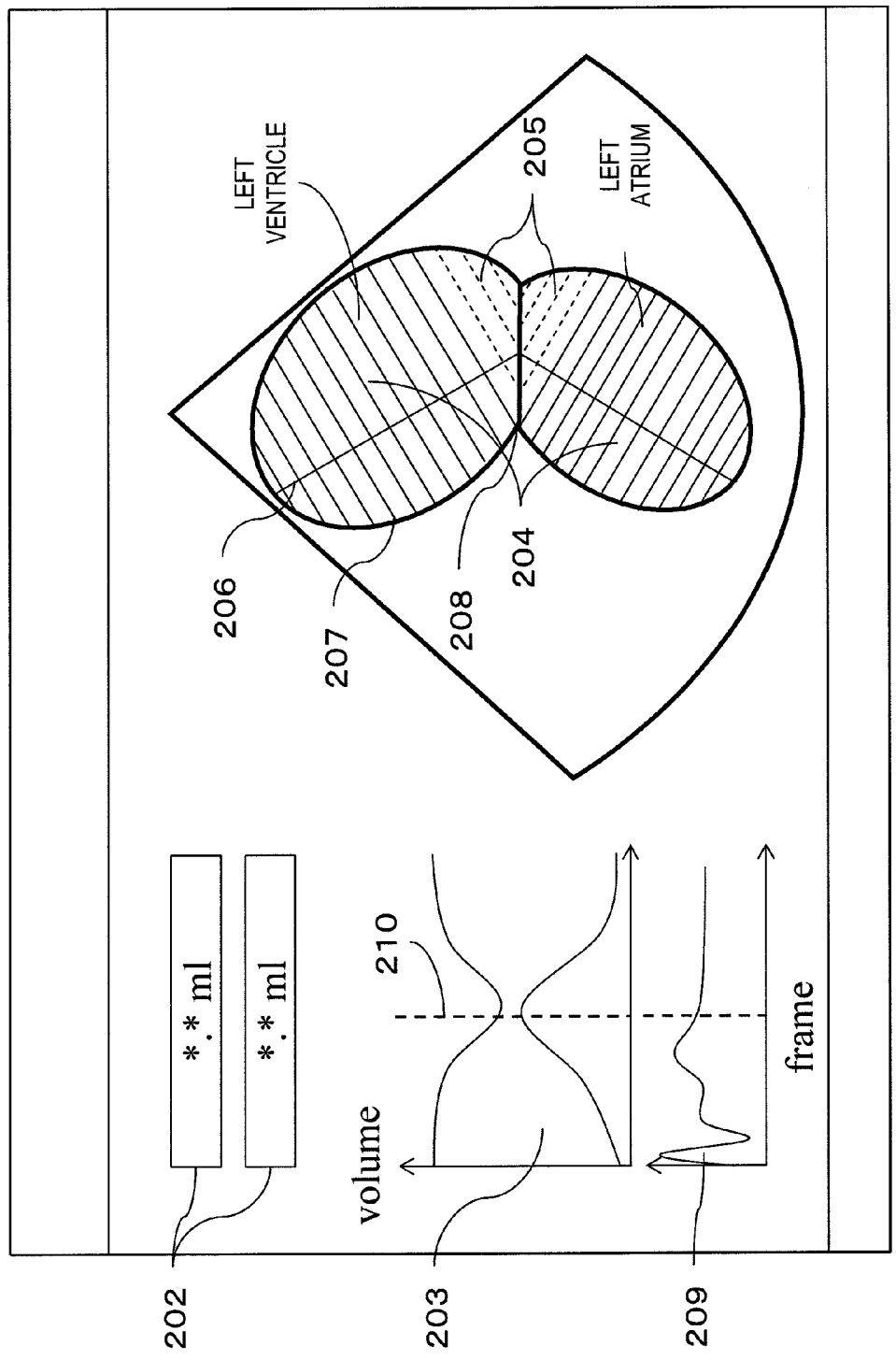
FIG. 2 shows an example of the ultrasonic tomographic image on which a left ventricle and a left atrium are drawn.

Next, operation to be executed by the examiner for acquiring volume of a cardiac chamber will be briefly described referring to FIG. 2. FIG. 2 shows an example of the ultrasonic image on which a left ventricle and a left atrium are drawn. The examiner first makes the image including the cardiac chamber to be measured drawn on a measurement screen based on the volume measurement by the conventional disk method. Next, the examiner traces the contour of the position equivalent to the inner wall surface of the cardiac chamber using an input device via the cardiac chamber trace specifying section 51. The tracing may be executed manually by the examiner or automatically by the device using the commonly known method.

When the tracing is completed and an inner wall trace line 207 of the cardiac chamber is generated, a valve ring line 208 or a cardiac chamber axis 206 is automatically generated by the device. Further, a disk formed by partition lines 204 which are orthogonal to a cardiac chamber axis 206 and a virtual disk formed by a virtual partition lines 205 are generated, and the volume is calculated. The calculated volume is outputted and displayed on a measurement screen. Manual tracing may be carried out by the examiner up to the virtual tracing.

In this manner, measurement of the cardiac chamber volume can be executed easily and accurately using the measurement operation method having the unaltered procedure as the conventional disk method. The detail of the process for acquiring volume of a cardiac chamber will be described below.

Figure 3:
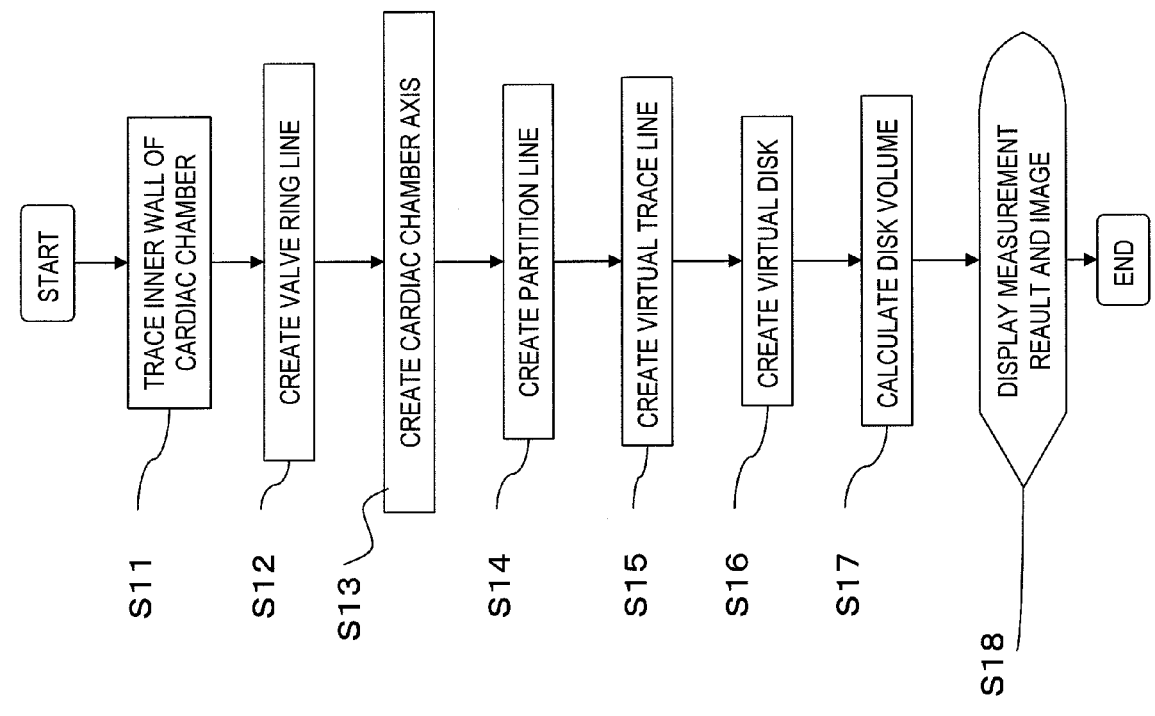
FIG. 3 shows processing flow for acquiring volume of a cardiac chamber in the present embodiment.

FIG. 3 shows the processing flow related to the present embodiment for acquiring volume of a cardiac chamber. As shown in FIG. 3, a cardiac chamber inner wall trace line 207 is first generated by tracing the contour equivalent to the inner wall surface of the cardiac chamber by the examiner (S11). For example, the contour equivalent to the inner wall of the cardiac chamber is traced by cardiac chamber trace specifying section 51 using the input device. The contour to be traced is from the valve ring portion of the cardiac chamber to its facing valve ring portion. The tracing may be carried out automatically by the device using the commonly known method. Also, two trace lines of the left ventricle and the left atrium may be set and measured simultaneously as shown in FIG. 2.

Next, a valve ring line 208 equivalent to the valve ring surface is to be generated by connecting both ends of the inner wall trace line of the cardiac chamber (S12). Then the cardiac chamber axis 206 is generated passing through the center of the valve ring surface 208 and the point in the inner wall trace line 207 of the cardiac chamber which is farthest from the center of the valve ring surface (S13). A plurality of partition lines 204 are generated being orthogonal to the cardiac chamber axis 206 and segmentizing the cardiac chamber region (S14).

Next, a virtual trace line 501 is generated by the virtual trace line generation section 31 (S15). In other words, it is assumed that the cardiac chamber axis 206 is to be vertical to the valve ring line 208 in the disk method, as shown in the left part of FIG. 4. After the position from one end of the valve ring to the other facing end of the valve ring is traced, the cardiac chamber axis 206 is set so as to connect the midpoint of the valve ring line 208 and the position on the inner wall trace line 207 which is farthest from the midpoint. The diameter of the disk which is formed by the partition lines 204 is set in the direction vertical to the cardiac chamber axis. The summation of the volume of the created disks is obtained as the volume of the cardiac chamber. In the expression 1, Di represents the diameter of disk, L represents the length of the cardiac chamber axis and N represents the number of disks for obtaining volume V. Generally, calculation is performed by N=20.

$$V = \frac{\pi}{4} \sum_{i=1}^{N} D_i^2 \cdot \frac{L}{N}$$ [Expression 1]

However, there are often cases in which it is difficult to perform a standard type of imaging of a heart depending on the clinical condition of an object or the incident angle of a probe. Since the cardiac chamber axis 206 is tilted in the direction which is not orthogonal to the valve ring line 208 as shown in the right part of FIG. 4, the disk of the shape presumed by the disk method cannot be created.

Figure 4:
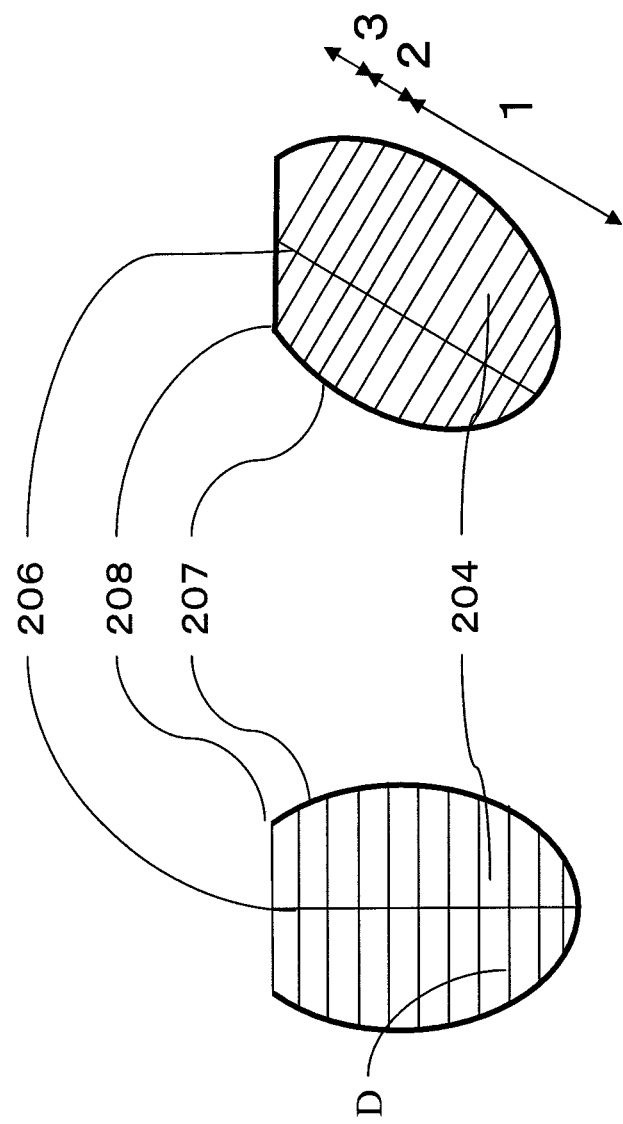
FIG. 4 is for explaining the difference in disk shapes between the case that a cardiac axis is orthogonal to a valve ring surface (left) and the case that they are not orthogonal to each other (right) in the disk method.

At this time, while the disk is created wherein both ends of the partition lines 204 intersect with the cardiac chamber inner wall trace line 207 while being sandwiched by the trace line in section 1 in the right part of FIG. 4, since one end of the partition lines 204 intersects with the inner wall trace line 207 of the cardiac chamber but the other end intersects with the valve ring line 208 which makes the diameter of the disk to be discontinued by the valve ring line 208 in section 2, the size of the disk becomes smaller than the actual size and the volume of the cardiac chamber is calculated smaller than the actual value. The volume is not calculated in section 3, since the cardiac chamber axis 206 is discontinued and the disk cannot be created.

In the present embodiment, since the inner wall trace line 207 of the cardiac chamber is always discontinued by the valve ring portion, a virtual disk is created which fills the region of sections 2 and 3 in the right part of FIG. 4 by virtually extending the discontinued sections, so as to improve the disk method to calculate the volume value with higher accuracy.

Figure 5:
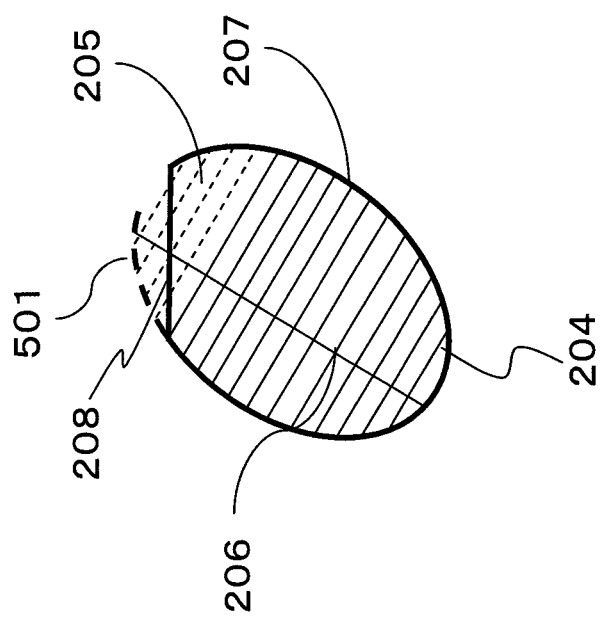
FIG. 5 shows generation of a virtual disk by acquiring virtual trace lines by extrapolation.

FIG. 5 shows the method that extrapolates the virtual trace line 501 based on the inner wall trace line 207 of the cardiac chamber. Virtual trace line 501 is generated between the inner wall trace line 207 of the cardiac chamber and the cardiac chamber axis 206 that form a second cardiac chamber region, being opposite to the lines. As an example, while the inner wall trace line 207 of the cardiac chamber is the assembly of points, the virtual trace lines are generated by, for example replacing the trace line with a curve function such as the spline and calculating the further portion of the point where the inner wall trace line of the cardiac chamber is discontinued using extrapolation calculation.

In this manner, while the inner wall trace line 207 of the cardiac chamber is discontinued by the valve ring portion in FIG. 5, virtual trace lines 501 (dotted-line part) are generated by extrapolation. In other words, the virtual trace lines 501 are set by extrapolating and extending the inner wall trace line 207 of the cardiac chamber from one end point of the inner wall trace line 207. One end point of the inner wall trace line 207 here is the end point of the side where the line orthogonal to cardiac chamber axis 206 intersects with the valve ring line 208. The virtual trace lines 501 may have the shape being connected to both ends of the inner wall trace line 207 of the cardiac chamber and closed, depending on image processing method. The virtual trace lines 501 extended from one end point of the inner wall trace line 207 of the cardiac chamber end at the point that intersect with the line starting from the other end point of the inner wall trace line 207 which is orthogonal to cardiac chamber axis 206.

Next, the virtual disk is created by disk creation section 32 (S16). As previously mentioned, when the virtual trace line 501 is generated, a virtual disk is created by a plurality of the virtual partial lines 205 that are between the virtual trace line 501 and the inner wall trace line 207 of the cardiac chamber which is axisymmetrical to the cardiac chamber axis 206 and that are orthogonal to the cardiac chamber axis 206. In other words, the virtual partition lines 205 are orthogonal to the cardiac chamber axis, wherein one end intersects with the virtual trace line 501 and the other end intersects with the inner wall trace line 207 of the cardiac chamber. Also, the virtual disk is created based on the virtual trace line 501, the virtual partition lines 205 and the inner wall trace line 207 of the cardiac chamber. The virtual disk is the partial disk necessary for volume calculation of the part being cut off obliquely by the valve ring surface which is the side including the inner wall trace line 207 of the cardiac chamber.

Figure 6:
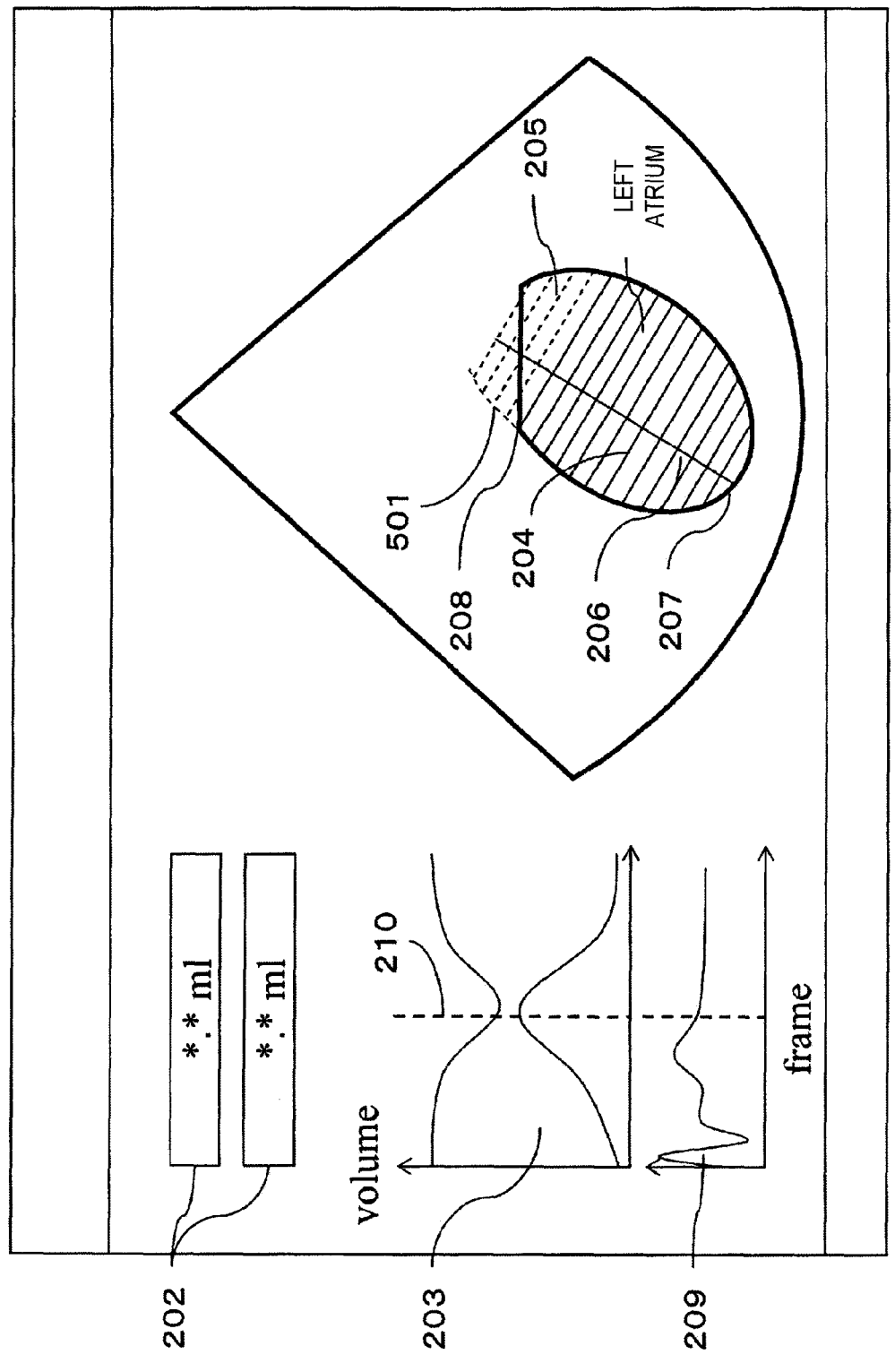
FIG. 6 shows GUI of correction mode for fine-adjusting virtual trace lines manually.

When the virtual trace line 501 and the disk are generated and the result is not satisfactory, it is possible to perform fine-adjustment of the virtual trace line 501 manually. FIG. 6 shows GUI of correction mode for fine-adjusting the virtual trace line 501 manually. When the correction mode shown in FIG. 6 is turned on, the virtual trace line 501, the cardiac chamber axis 206 and the virtual partition lines 205 are displayed. The examiner adjusts the position or length of the virtual trace line 501 to modify the shape of the line by operating the input device. Following the procedure, since the position or length of the virtual partition lines 205 are also changed and along with the shape of the virtual disk, change of the virtual partition lines 205 is also displayed on the screen in real time simultaneously with the operation executed by the examiner. Since the volume value is changed along with the shape change of the disk, the volume is re-calculated simultaneously and displayed on cardiac chamber volume measurement value 202.

Next, the volume of the disk is calculated by the volume calculation section 33 and the summation of the calculated volumes is obtained as volume of the cardiac chamber (S17). The region equivalent to section 1 in FIG. 4, which is the region formed by a plurality of the partition lines 204 wherein both ends intersect with the inner wall trace line 207 of the cardiac chamber (a first cardiac chamber) is obtained by the conventional disk method. On the other hand, the region equivalent to section 2 and section 3 in FIG. 4 which is the region encompassed by the partition line closest to the valve ring line 208 from among the plurality of partition lines wherein both ends intersect with the inner wall trace line 207 of the cardiac chamber, the valve ring line 208 and the inner wall trace line 207 of the cardiac chamber (a second cardiac chamber) must be calculated using the pseudo disk method as the volume of the partial disk which is cut off obliquely as shown in the upper stage of FIG. 7.

Figure 7:
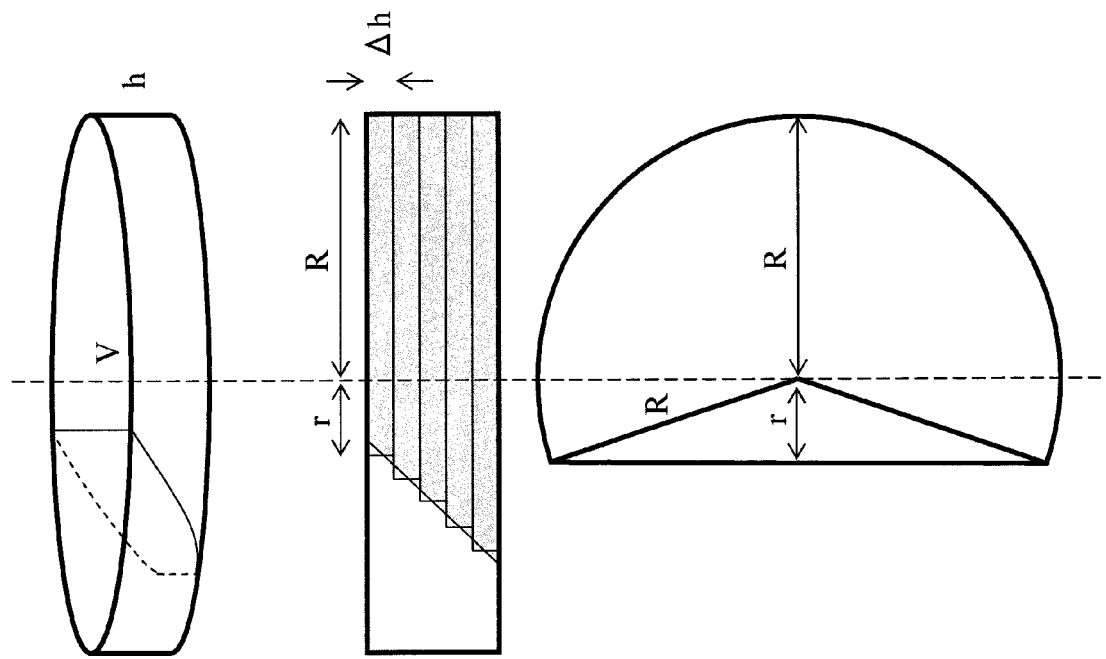
FIG. 7 shows the calculation method for calculating volume of a partial disk wherein a virtual disk is obliquely cut off, using the disk method with micro-height.

That is, the region of which the volume is actually calculated is the region having a cross-section of trapezoidal shape shown on the right side of the middle part in FIG. 7. This region is further divided into thin disks having height $\Delta h$. Volume of the thin disk is obtained as shown in the lower part of FIG. 7. The lower part of FIG. 7 indicates the top surface of the disk.

By using radius R from the center of the disk and distance r from the center of the disk to the cut surface of the disk, area of base of the disk can be obtained by the sum of the sector form and triangular form. Volume of the thin disk can be calculated by multiplying the obtained base area by micro-height $\Delta h$. By obtaining the volumes of the divided multiple thin disks and the summation of them, the volume value of the disk can be determined.

By executing the above-described calculation in all of the virtual disks equivalent to sections 2 and 3 in FIG. 4 and adding them to the volume of section 1, volume of the entire cardiac chamber can be calculated.

While processing of the volume calculation in one frame of image is described above, it is desirable to measure continuous volume change since a heart is a moving organ. By repeating the above-described steps for every frame, the volume value of each frame is calculated, thus the volume change can be obtained. However, since manual tracing of the inner wall of the cardiac chamber for each frame is cumbersome and complicated, the inner wall trace line 207 which is traced in the first frame may be tracked by the trace line tracking calculation section 34. In this manner, there is no need to execute manual tracing after the second frame, since the inner wall trace line 207 of the cardiac chamber is modified as fitting the contour in accordance with the modification of the contour in the inner wall of the cardiac chamber. Steps 12~17 are automatically executed in each frame after the second frame, and volume value for each frame is calculated.

Finally, the volume value and the image are outputted and displayed by image display section 61 (S18). FIG. 2 shows the step wherein both of a left ventricle and a left atrium are traced and the volumes and the time variation thereof are measured. On the cardiac chamber volume measurement value 202, the volume value of a first cardiac chamber region calculated by the first disk method, volume value of a second cardiac chamber region calculated by the pseudo disk method, and the entire volume value by the sum of the volume values of the first and second cardiac chamber regions are displayed with respect to the left ventricle and the left atrium.

Input setting is to be executed so that at least one of the volume values is to be displayed on the display unit 6, by inputting a desired volume value from among the volume values of the first region, the second region and the entire volume region via the input unit 5. In this manner, at least one of the respective volumes can be displayed on the display unit. On a cardiac chamber volume variation graph 203, the volume variation graph of the left ventricle and the left atrium are displayed. Also, a biological signal 209 is also displayed in parallel with other graphs.

Also on an ultrasonic image, the inner wall trace line 207 of a cardiac chamber, the cardiac chamber axis 206, the valve ring line 208, the partition lines 204 and the virtual partition lines 205 are superimposed and displayed. In this manner, the position which is not possible to be measured by the conventional disk method can be measured by displaying the virtual partition lines 205. Also, measurement of the position which is not possible to be measured using the conventional disk method can be indicated by displaying the virtual trace line 501.

The ultrasonic image, the inner wall trace line 207 of the cardiac chamber, the cardiac chamber axis 206, the valve ring line 208, the partition lines 204, the virtual partition lines 205, the graphs, etc. shown in FIG. 2 are displayed being synchronized with the cardiac motion of the object.

A time phase bar 210 on the graph indicates the position of the phase of the ultrasonic image.

As described above, in accordance with the present embodiment, it is possible to measure the volume in the vicinity of a valve ring which used to be measured smaller than the actual volume, with higher accuracy. Also, since the measurement procedure is the same as the conventional method, the measurement can be executed easily and quickly without increasing the operation steps. Further, since the position of the virtual trace line 501 or the virtual partition lines 205 are outputted and displayed, the measurement can be executed while confirming the position of the disk which fills a cardiac chamber.

(Virtual Trace Line Generation Method: Variation 1)

Figure 8:
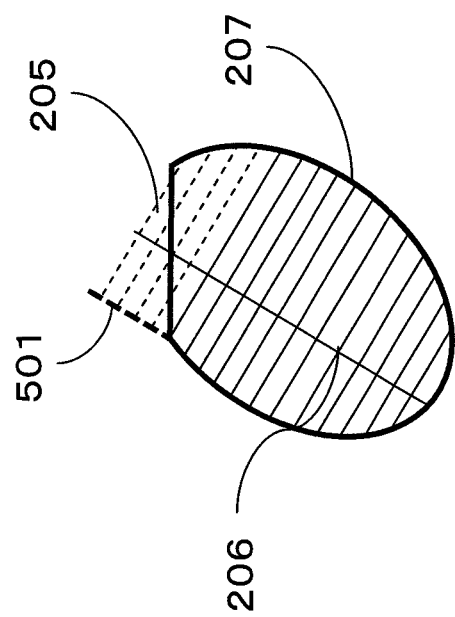
FIG. 8 shows modification example 1 in generation of a virtual trace line.

Next, a variation of the method for generating a virtual trace line will be described. FIG. 8 shows variation example 1 for generating virtual trace line 501. As shown in FIG. 8, the virtual trace line 501 which is parallel to cardiac chamber axis 206 is generated from an endpoint of the inner wall trace line 207 of a cardiac chamber. A virtual disk is created between the generated virtual trace line and its facing cardiac chamber trace line.

In other words, the virtual trace line 501 is set by extending a straight line which is parallel to the cardiac chamber axis 206 from one end of the inner wall trace line 207 of the cardiac chamber. In accordance with the above-described method, the virtual trace line 501 can be set easily and quickly with less calculation amount.

(Virtual Trace Line Generation Method: Variation 2)

Figure 9:
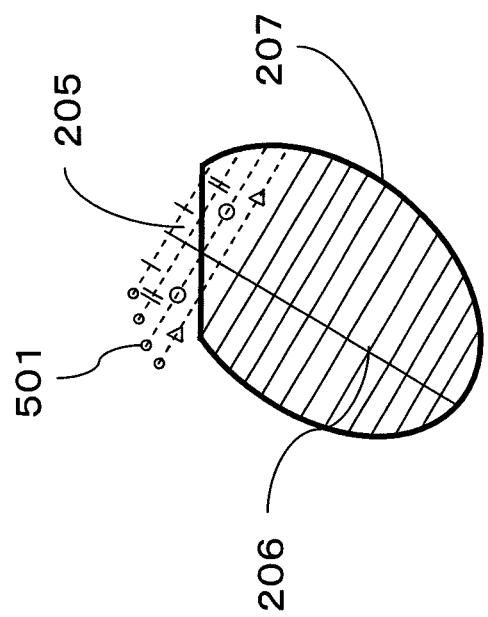
FIG. 9 shows modification example 2 in generation of a virtual trace line.

Next, variation example 2 of the method for generating a virtual trace line will be described. FIG. 9 shows variation example 2 for generating virtual trace line 501. As shown in FIG. 9, the virtual trace line 501 is generated at the position which is axisymmetrical to the cardiac chamber axis 206 of the cardiac chamber inner wall trace line 207. The virtual partition lines 205 are generated between the generated the virtual trace line 501 and the inner wall trace line 207 of the cardiac chamber.

In other words, the virtual trace line is generated at the position which is axisymmetrical to the cardiac chamber axis 206 of the cardiac chamber inner wall trace line 207 that forms the second cardiac chamber region. In accordance with the above-described method, the virtual trace line can be set easily and quickly with less calculation amount.

(Virtual Trace Line Generation Method: Variation 3)

Figure 10:
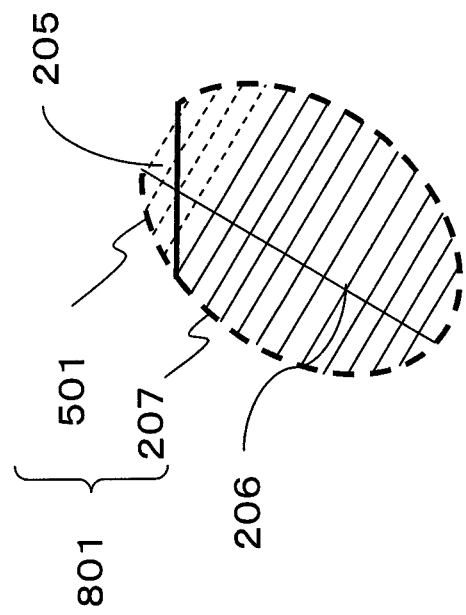
FIG. 10 shows modification example 3 in generation of a virtual trace line.

Next, variation example 3 of the method for generating a virtual trace line will be described. FIG. 10 shows variation example 3 for generating the virtual trace line 501. As shown in FIG. 10, contour line 801 is generated by connecting and integrating the cardiac chamber inner wall trace line 207 and the virtual trace line 501. A contour line 801 is modified by the contour transformation algorithm such as the dynamic contour model or the contour pattern matching. The entire contour line 801 is extracted while fitting the trace line part of the cardiac chamber to the contour of the cardiac chamber by the effect of the contour model and controlling the contour of the virtual trace part.

The disk is created in the region sandwiched by the extracted contour line.

In accordance with the above-described method, a balanced and natural form of virtual trace line can be generated while considering the form of the cardiac chamber trace line.

(Virtual Trace Line Generation Method: Variation 4)

Figure 11:
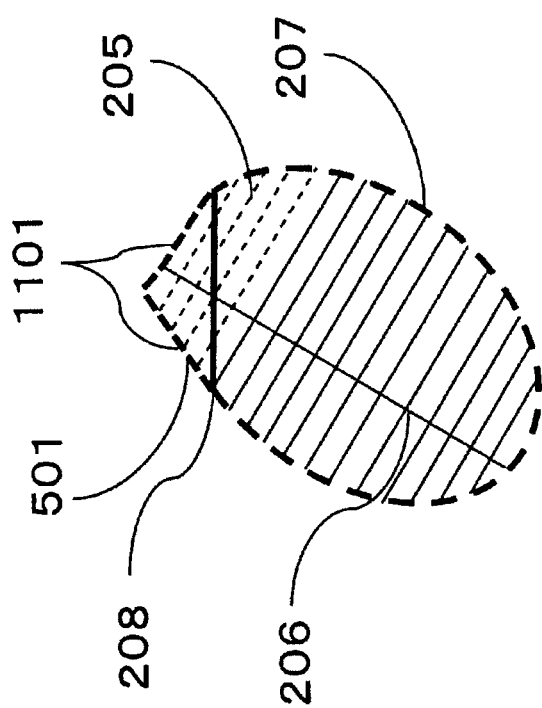
FIG. 11 shows modification example 4 in generation of a virtual trace line.

Next, variation example 4 of the method for generating a virtual trace line will be described. FIG. 10 shows variation example 4 for generating the virtual trace line 501. It is the method to close the virtual trace line 501 along the form of the valve as shown in FIG. 11. The left atrium and the valve have the form that they are integrated with each other and closed, since a valve 1101 closes when the blood flows from the pulmonary artery to the left atrium. At this time, the volume of the valve part region can be measured in addition to the volume of the left atrium if the inner wall trace line 207 of the cardiac chamber is set in accordance with the form of the valve. Also, the volume of the region encompassed by the valve and the valve ring line and the volume of the region encompassed by the cardiac chamber inner wall surface of the left atrium and the valve ring surface can be measured separately by marking them off by the valve ring line 208. Further, since the volume of the portion wherein the valve is intruded inside of the left ventricle can be subtracted by subtracting the volume of the region encompassed by the valve and the valve ring surface from the volume of the region encompassed by the cardiac chamber inner wall surface of the left ventricle and the valve ring surface, it is possible to measure the volume of the left ventricle at late in systole with higher accuracy.

In accordance with the above-described method, it is possible to calculate the volume with higher accuracy even in the case that the volume is defined including the region encompassed by the valve.

(Variation 1: Virtual Disk Volume Calculation Method)

Figure 12:
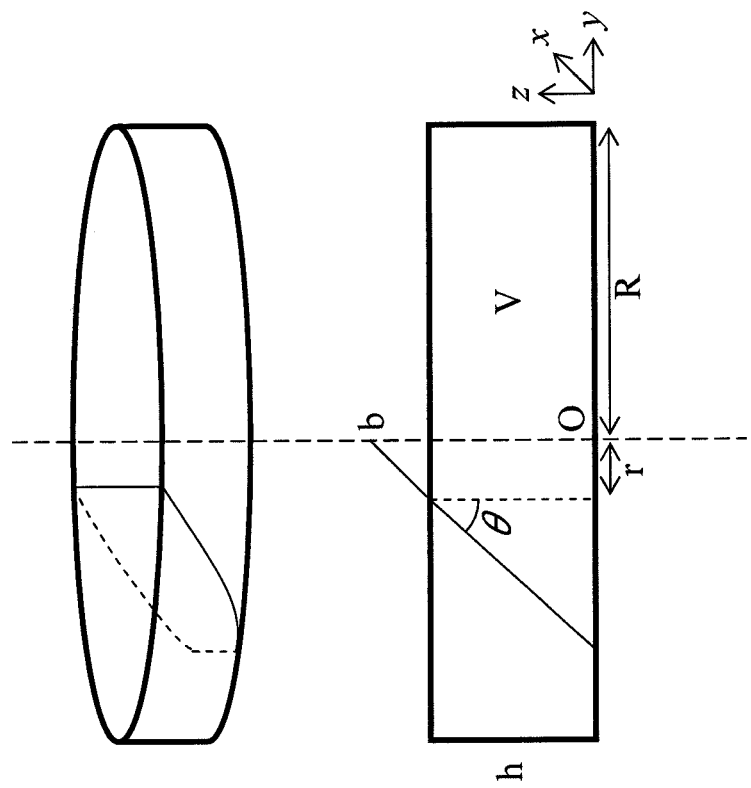
FIG. 12 shows modification example 1 of the method for calculating volume of a virtual disk.

Next, variation example 1 of the method for calculating volume of a virtual disk will be described. FIG. 12 shows variation example 1 of the method for calculating volume of a virtual disk, which is the variation of the disk volume calculation step (S14) by the volume calculation section 33. This variation executes holomorphic calculation by the integral calculus for calculating the disk volume which is cut off obliquely shown in the upper part of FIG. 12.

The lower part of FIG. 12 is the lateral view of the disk. The volume of the partial disk region can be determined by the expression 2, by setting the radius of the disk as R, the length from the center of the disk to the cut surface as r, cutting angle as θ, and height of the disk as h.

$$\begin{cases} x^2 + y^2 \leq R^2 \\ 0 \leq z \leq h \ (y \geq -r) \\ 0 \leq z \leq y\dfrac{1}{\tan \theta} + b \ (y \leq -r) \end{cases}$$ [Expression 2]

Volume V of the partial disk can be determined by calculating the volume of the region encompassed using the expression 2 using the integral calculus. By executing the expression 2 on all of the virtual disks and summing the obtained volumes, volume of the cardiac chamber can be calculated.

In accordance with the above-described method, volume of a cardiac chamber can be calculated easily and quickly without using complicated calculation such as figure decomposition, since holomorphic calculation can be performed by the integral calculus.

While the disk method of a single plane is described above with respect to the process for determining volume of a cardiac chamber, the present embodiment can also be applied, for example to the biplane disk method by four-chamber view of a cardiac apex and two-chamber view of a cardiac apex. In this case, while the disk pattern will be an elliptic cylinder since the disk diameter of four-chamber view and two-chamber view are different in general, only modification to be made is to replace the columnar calculation in the above-described embodiment with the elliptical calculation. The present invention can also be applied to other organs besides a heart in the case that the form of the organ can be represented by convergence of an elliptic cylinder.

Also, the medical image display device of the present invention is for displaying the tomographic image acquired by scanning a cross section of a heart of an object on display unit 6 and obtaining volume of the cardiac chamber region encompassed by the cardiac chamber inner wall surface and the valve ring surface of the heart based on the displayed tomographic image, which can be configured to display a cardiac chamber contour line formed by inner wall trace line 207 of the cardiac chamber equivalent to the cardiac chamber inner wall surface and the valve ring line 208 equivalent to the valve ring surface, the cardiac chamber axis 206 passing through the center of the valve ring line 208 and the position in the inner wall trace line 207 which is farthest from the center and a plurality of partition lines that are orthogonal to the cardiac chamber axis 206 on the display unit 6.

In this case, by setting the region where both ends of the partition lines intersect with inner wall trace line 207 of the cardiac chamber as a first cardiac chamber region and the region where one end of the partition lines intersect with the valve ring line 208 and the other end intersects with the inner wall trace line 207 as a second cardiac chamber region, it is possible to display the first cardiac chamber region and the second cardiac chamber region in different display patterns. In this manner, an examiner can recognize that volumes of the first and second cardiac chambers are calculated as different regions.

More specifically, by setting a plurality of partition lines in the first cardiac chamber region as first partition lines and a plurality of partition lines in the second cardiac chamber as second partition lines, it is possible to display the first partition lines and the second partition lines, for example in different colors to make their display patterns different.

Also, by respectively displaying volumes of the first cardiac chamber and the second cardiac chamber, the examiner can recognize that the volumes of the respective cardiac chambers are calculated as different regions. In this case, by executing numeric display of volumes of the first and second cardiac chambers by the color corresponding to the color of the plurality of the first and second partition lines, the examiner can easily relate the volume to the respective regions.

Further, by displaying virtual trace line 501 which forms the second cardiac chamber region which is facing the region sandwiched by the cardiac chamber inner trace line 207 and the cardiac chamber axis 206 and a plurality of the virtual partition lines 205 wherein one end intersects with the virtual trace line 501 and the other end intersects with the inner wall trace line 207 and also are orthogonal to the cardiac chamber axis 206, the examiner can recognize that volume of the second cardiac chamber region is calculated using the pseudo disk method.

While the case for calculating volume of a heart is exemplified in the above-described embodiment, the present invention can be applied to the organs of which the inner cavity can be measured such as a bladder, prostate gland, liver and pancreas. In these cases, since the organs do not have a valve ring surface like a heart does, an inner cavity wall surface which is orthogonal to the inner cavity wall takes place of the valve ring surface. In these organs as in the same manner as a heart, in the case that the volume is calculated smaller than the actual volume or the disk cannot be created when the conventional disk method is used, the entire volume of such regions can be calculated with high accuracy using the pseudo disk method.

DESCRIPTION OF REFERENCE NUMERALS

1: ultrasonic signal generation unit, 2: ultrasonic image generation unit, 3: calculation unit, 4: storage unit, 5: input unit, 6: display unit, 7: control unit, 12: ultrasonic signal transmission/reception section, 21: 2-dimensional cross-sectional image generation section, 31: virtual trace line generation section, 32: disk generation section, 33: volume calculation section, 51: cardiac chamber trace specification section, 204: partition line, 205: virtual partition line, 206: cardiac chamber axis, 207: cardiac chamber inner wall trace line, 208: valve ring line, 501: virtual trace line, 801: contour line

The invention claimed is:
1. A medical image display method that displays the tomographic image acquired by scanning a cross section of a heart in an object to be examined on a display unit and obtains a volume of a cardiac chamber region encompassed by an inner wall surface of a cardiac chamber and a valve ring surface based on the displayed tomographic image, comprising:
 a step of tracing and displaying a portion equivalent to the inner wall surface of the cardiac chamber on the tomographic image;
 a step of displaying a valve ring line equivalent to the valve ring surface connecting both end points of the traced cardiac chamber inner wall trace line;
 a step of displaying an inner cavity axis passing through the center of the valve ring line and the position in the cardiac chamber inner wall trace line which is the farthest from the center of the valve ring line;
 a step of displaying a plurality of partition lines which is orthogonal to the cardiac chamber axis and of which their both ends intersect with the cardiac chamber inner wall trace line;
 a step of calculating a cardiac chamber volume of a first cardiac chamber region formed by the plurality of partition lines using the disk method;
 a step of calculating a cardiac chamber volume of a second cardiac chamber region encompassed by the partition line which is the closest to the valve ring line from among the plurality of partition lines, the valve ring line and the cardiac chamber inner wall trace line;

a step of calculating the entire cardiac chamber volume by the sum of the calculated volumes of the calculated first and second cardiac chamber regions; and a step of displaying the cardiac chamber volume of the first and second cardiac chamber regions and/or the volume of the entire cardiac chamber region.

2. The medical image display method according to claim 1, wherein the step of calculating the cardiac chamber volume of the second cardiac chamber region by the pseudo disk method comprises:

a step of generating a virtual trace line which forms the second cardiac chamber region facing the region sandwiched by the cardiac chamber inner wall trace line and the cardiac chamber axis;

a step of generating a plurality of virtual partition lines which are orthogonal to the cardiac chamber axis, and their one end intersects with the virtual trace line and the other end intersects with the inner wall trace line of the cardiac chamber;

a step of generating a virtual disk based on the virtual trace line, the virtual partition lines and the cardiac chamber inner wall trace line; and a step of cutting the virtual disk by the valve ring surface and calculates a volume of the partial disk of the side including the cardiac chamber inner wall trace line as cardiac chamber volume of the second cardiac chamber region, wherein the virtual trace line and the virtual partition lines are displayed on the display unit.

3. The medical image display method according to claim 2, wherein the step of generating the virtual trace line generates a virtual trace line by extending and extrapolating a cardiac chamber trace line from one end point of the cardiac chamber inner wall trace line using the cardiac chamber inner wall trace line itself as a curve function.

4. The medical image display method according to claim 2, wherein the step of generating the virtual trace line generates a virtual trace line by extending a straight line which is parallel to the cardiac chamber axis from one end point of the cardiac chamber inner wall trace line.

5. The medical image display method according to claim 2, wherein the step of generating the virtual trace line generates a virtual trace line at the position which is axisymmetrical to the cardiac chamber axis of the cardiac chamber inner wall trace line forming the second cardiac chamber region.

6. The medical image display method according to claim 2, wherein the step of generating the virtual trace line integrates the cardiac chamber inner wall trace line with the virtual trace line using the contour curve function.

7. The medical image display method according to claim 2, wherein the step of calculating the cardiac chamber volume of the second cardiac chamber region segmentizes the partial disk into a plurality of micro-height disks and calculates the cardiac chamber volume by the summation of the volumes of the plurality of disks.

8. The medical image display method according to claim 1, wherein the step of calculating the cardiac chamber volume of the second cardiac chamber region calculates the volume of the second cardiac chamber using integral calculus.

9. A medical image diagnostic apparatus comprising:

a display unit configured to display a tomographic image acquired by scanning a cross section of a heart in an object to be examined; and a calculation unit configured to obtain volume of a cardiac chamber region encompassed by a cardiac chamber inner wall surface of the heart based on the tomographic image displayed on the display unit, wherein the calculation unit comprises:

means to trace a portion equivalent to the cardiac chamber inner wall surface of the heart on the tomographic image displayed on the display unit;

means to generate and display a valve ring line equivalent to the valve ring surface that connects both end points of the traced cardiac chamber trace line;

means to generate and display the cardiac chamber axis passing through the center of the valve ring line and the position in the cardiac chamber inner wall trace line which is the farthest from the center of the valve ring line;

means to generate and display a plurality of partition lines which is orthogonal to the cardiac chamber axis and of which their both ends intersect with the cardiac chamber inner wall trace line;

means to calculate inner cavity volume of a first cardiac chamber region formed by the plurality of partition lines using the disk method;

means to calculate cardiac chamber volume of a second cardiac chamber region encompassed by the partition line which is the closest to the valve ring line from among the plurality of partition lines, the line and the cardiac chamber inner wall trace line using the pseudo disk method;

means to calculate volume of the entire cardiac chamber by adding the calculated volumes of the first cardiac chamber region and the second cardiac chamber region; and means to display the cardiac chamber volume of the first and second cardiac chamber regions and/or the volume of the entire cardiac chamber.

10. A medical image display device that displays the tomographic image acquired by scanning a cross section of a heart of an object to be examined and obtains a volume of a cardiac chamber region encompassed by a cardiac chamber inner wall surface and a valve ring surface of the heart based on the displayed tomographic image, the medical image display device comprising:

a calculation unit for calculating a cardiac chamber contour line formed by a cardiac chamber inner wall trace line equivalent to the cardiac chamber inner wall surface and a valve ring line equivalent to the valve ring surface of the medical image, a cardiac chamber axis passing through the center of the valve ring line and the position in the cardiac chamber inner wall trace line which is the farthest from the center of the valve ring line, an image on which a plurality of partition lines orthogonal to the cardiac chamber axis, and a first cardiac chamber region in which both ends of the partition lines intersect with the cardiac chamber inner trace line, and a second cardiac chamber region in which one end of the partition lines intersects with the valve ring line and the other end of the partition lines intersects with the cardiac chamber inner wall trace line; and a display unit for displaying the first cardiac chamber region and the second first cardiac chamber region in different display patterns.

11. The medical image display device according to claim 10, wherein the calculation unit calculates the plurality of partition lines in the first cardiac chamber region as first partition lines and the plurality of partition lines in the second cardiac chamber region as second partition lines, and wherein the display unit displays the first partition lines and the second partition lines in different display patterns on the medical image.

12. The medical image display device according to claim 10, wherein the calculation unit calculates a numerical value of volume of the first cardiac chamber region and numerical values of volume of the second cardiac chamber region corresponding to the display patterns of the first cardiac chamber region and the second cardiac chamber region, respectively, or to the display patterns of the plurality of first partition lines and the plurality of second partition lines while the volumes, respectively.

13. The medical image display device according to claim 10, wherein the calculation unit calculates a virtual trace line forming the second cardiac chamber region which is facing the region sandwiched by the cardiac chamber inner wall trace line and the cardiac chamber axis, and a plurality of virtual partition lines which are orthogonal to the cardiac chamber axis and their one end intersects with the virtual trace line and the other end intersects with the cardiac chamber inner wall trace line on the medical image.

14. A medical image display method that displays the tomographic image acquired by scanning a cross section of an organ in an object to be examined on a display unit and obtains a volume of the inner cavity region encompassed by an inner wall surface of the inner cavity in the organ based on the displayed tomographic image, the method comprising:
    a step of tracing and displaying a portion equivalent to the inner wall surface of the inner cavity on the tomographic image;
    a step of displaying a line connecting both end points of the traced inner cavity trace line;
    a step of displaying an inner cavity axis passing through the center of the line and the position in the inner cavity trace line which is the farthest from the center of the line;
    a step of displaying a plurality of partition lines which is orthogonal to the inner cavity axis and of which their both ends intersect with the inner cavity trace line;
    a step of calculating an inner cavity volume of a first inner cavity region formed by the plurality of partition lines using the disk method;
    a step of calculating an inner cavity volume of a second inner cavity region encompassed by the partition line which is the closest to the line from among the plurality of partition lines, the line and the inner cavity trace line;
    a step of calculating the entire inner cavity volume by the sum of the calculated volumes of the first and second inner cavity regions; and
    a step of displaying the inner cavity volume of the first and second inner cavity regions and/or the volume of the entire inner cavity region.

15. A medical image diagnostic apparatus comprising:
    a display unit configured to display a tomographic image acquired by scanning a cross section of an organ in an object to be examined; and
    a calculation unit configured to obtain a volume of an inner cavity region encompassed by an inner cavity inner wall surface of the organ based on the tomographic image displayed on the display unit,
    wherein the calculation unit comprises:
    means to trace a portion equivalent to the inner cavity inner wall surface of the organ on the tomographic image displayed on the display unit;
    means to generate and display a line that connects both end points of the traced inner cavity trace line;
    means to generate and display the inner cavity axis passing through the center of the line and the position in the inner cavity trace line which is the farthest from the center of the line;
    means to generate and display a plurality of partition lines which are orthogonal to the inner cavity axis and of which their both ends intersect with the inner cavity trace line;
    means to calculate inner cavity volume of a first inner cavity region formed by the plurality of partition lines using the disk method;
    means to calculate an inner cavity volume of a second inner cavity region encompassed by the partition line which is the closest to the line from among the plurality of partition lines, the line and the inner cavity trace line using the pseudo disk method;
    means to calculate volume of the entire inner cavity by adding the calculated volumes of the first inner cavity region and the second inner cavity region; and
    means to display the inner cavity volumes of the first and second inner cavity regions and/or the volume of the entire inner cavity.

* * * * *